(12) United States Patent
Mollard et al.

(10) Patent No.: US 6,844,424 B1
(45) Date of Patent: Jan. 18, 2005

(54) METHOD FOR OBTAINING AVIAN BIOLOGICAL PRODUCTS

(75) Inventors: Laurent Mollard, Vannes (FR); Agnes Montillet, Saint Nazaire (FR); Cecile Horriere, Vannes (FR); Jack Legrand, Saint Nazaire (FR); Tan Hung Nguyen, Saint-Ave (FR)

(73) Assignee: Diana Ingredients, Saint Nolff (FR)

( * ) Notice: Subject to any disclaimer, the term of this patent is extended or adjusted under 35 U.S.C. 154(b) by 0 days.

(21) Appl. No.: 09/763,724

(22) PCT Filed: Aug. 27, 1999

(86) PCT No.: PCT/FR99/02052

§ 371 (c)(1),
(2), (4) Date: Feb. 27, 2001

(87) PCT Pub. No.: WO00/11969

PCT Pub. Date: Mar. 9, 2000

(30) Foreign Application Priority Data

Aug. 31, 1998 (FR) .............................. 98 10868

(51) Int. Cl.[7] .................. A61K 38/17; A61K 35/32; A23L 1/31

(52) U.S. Cl. .................. 530/356; 530/412; 530/422; 530/427; 426/518; 426/644; 426/645; 426/655; 424/489; 424/548; 424/549

(58) Field of Search ................. 530/356, 412, 530/422, 427; 426/518, 644, 645, 655; 424/489, 548, 549

(56) References Cited

U.S. PATENT DOCUMENTS

| | | | |
|---|---|---|---|
| 3,900,579 A | | 8/1975 | Masuda et al. ............. 426/388 |
| 5,384,149 A | * | 1/1995 | Lin ............................ 426/646 |
| 5,637,321 A | * | 6/1997 | Moore ........................ 424/489 |

* cited by examiner

*Primary Examiner*—Jon Weber
*Assistant Examiner*—Abdel A. Mohamed
(74) *Attorney, Agent, or Firm*—Foley & Lardner LLP

(57) ABSTRACT

This invention provides a method for separating and extracting biological products of avian origin. The method allows for the production of avian cartilages and of active ingredients which can be extracted from the cartilages thus obtained.

5 Claims, 1 Drawing Sheet

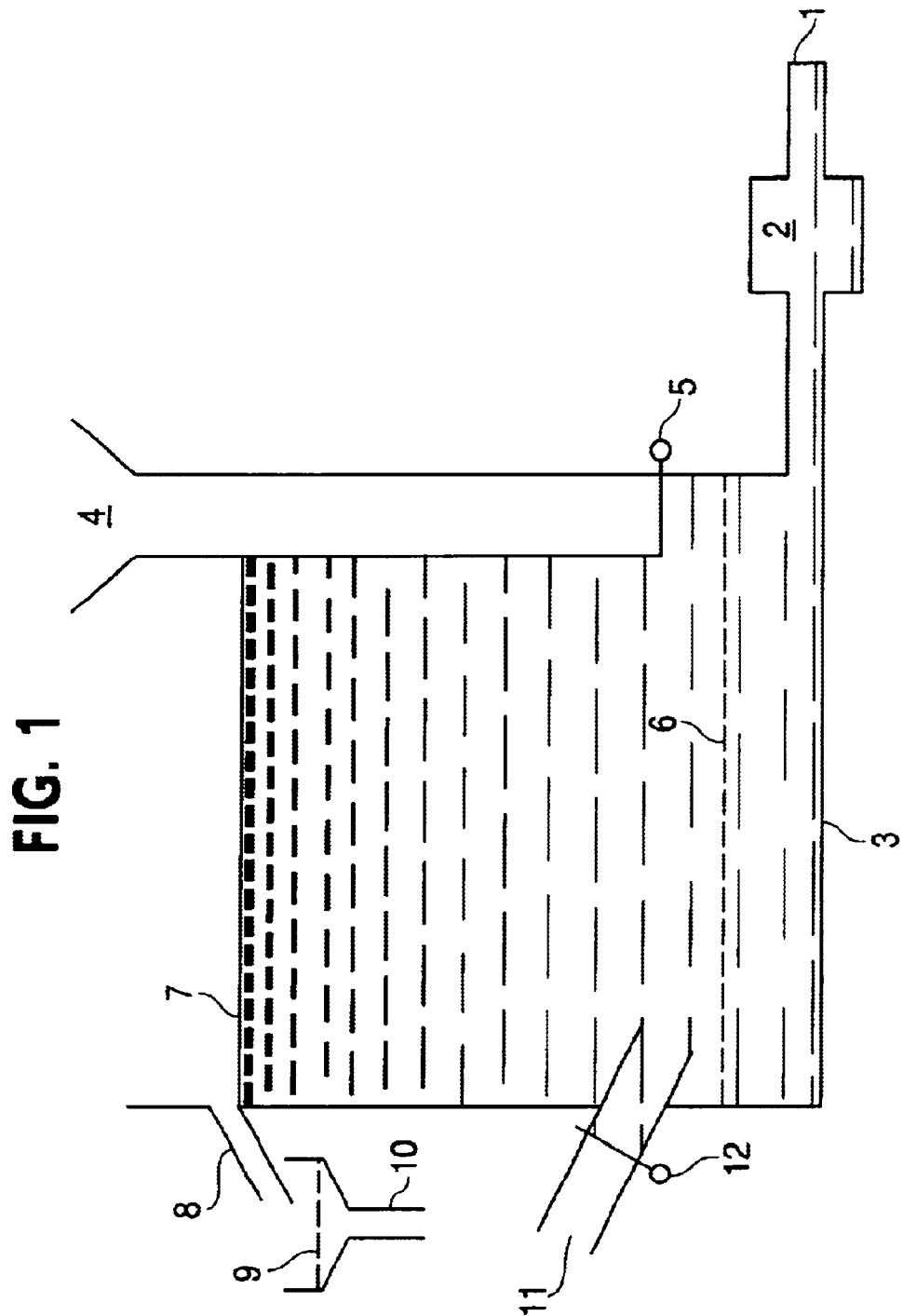

METHOD FOR OBTAINING AVIAN BIOLOGICAL PRODUCTS

The present invention relates to a method for separating and extracting biological products of avian origin. The method allows the production of avian cartilages and of active ingredients which can be extracted from the cartilages thus obtained.

STATE OF THE ART

Cartilages are complex tissues which are found in numerous organs in humans and animals.

Thus, it is possible to remove cartilages from the nasal septa, the larynx, the arterial trachea, the bronchi, the articular surfaces, the cartilages joining the long bones, the xiphoid process of the sternum, and the like.

In chondrichthian fish (shark, dogfish, skate, and the like), the entire skeleton is cartilaginous.

Cartilages consist of numerous molecules used as active ingredients in human and animal dietetic nutrition, in human and veterinary pharmacy or in cosmetology. Among the best known molecules, there may be mentioned: collagens, hexosamines and glycosaminoglycans (chondroitin sulfate, keratan sulfate, hyaluronic acid).

The majority of these molecules are up until now extracted from bovine cartilages. However, since the appearance of bovine spongiform encephalitis (BSE), the food, pharmaceutical and cosmetic industries have been worried about a possible contamination of these extracts by the prions which are responsible for BSE and which are difficult to detect.

The use of chondricthian fish skeletons may be a solution for replacing products of bovine origin. However, marine resources have quantitative, economic and environmental limits.

It is therefore useful to find another source of cartilages from animals which are abundant and which are recognized as being free of prion diseases. Domestic poultry (chickens, turkeys, ducks, guinea fowl, quails and pigeons) meet these criteria of sanitary safety.

On the skeleton of birds, the cartilages which can be used are found mainly on the process of the sternum (carina), on the articular surfaces, and at the level of the cartilages joining the long bones.

However, these cartilages represent only a very small part of the skeleton of birds and we do not know a process capable of separating them and extracting them efficiently for the purpose of industrial production. Thus, for example, patent U.S. Pat. No. 5,637,321 describes a manual removal, after dissection with a knife, of chicken cartilages which can be used to obtain type II collagen which is useful in the treatment of arthritis. Such a manual method does not allow mass industrial production.

INVENTION

We have invented a mechanized method which allows the separation and the extraction of cartilages from the skeletons of domestic fowl.

The method consists in grinding skeletons of domestic fowl and subjecting the ground material to a flow of liquid which circulates in a separating vessel. Advantageously, said liquid flow has an ascending vertical component.

It was found to be advantageous to grind the skeletons of fowl in order to obtain particles of less than about one centimeter in size.

The separating liquid which can be used may be simply water or brine consisting of water and an edible salt. In the latter case, cooking salt (NaCl) may be advantageously used to produce a brine containing less than 32.5% of salt.

The shape of the separating vessel as well as the height of the separating liquid are unimportant. What is essential is that the separating liquid should be able to flow freely. The flow rates of the separating liquid are adjusted according to the structure of the skeletons which may vary with the animal species and the age of the fowl. The size of the separating vessel should vary according to the quantities of products to be treated.

As nonexhaustive and nonlimiting examples, FIG. 1 as well as the following trials will make it possible to understand the invention more clearly.

FIG. 1

A cycle for separation and extraction of the cartilages occurs according to the principle in FIG. 1 (FIG. 1 does not give a scale or a dimension for the device).

The conduit 1 brings water or brine into the separating vessel 3 by means of the pump 2 which regulates the flow rate.

A ground product of poultry skeletons is introduced into the conduit 4, the valve 5 is opened, the ground product is allowed to descend as far as the bottom of the vessel 3 and above the grid 6.

The bone tissues remain on the grid 6 whose meshes are less than the size of the particles of ground skeletons. The cartilaginous tissues are carried by the separating liquid to the surface (7) thereof and are discharged by the overflow outlet 8. They are then collected in the sieve 9. The excess liquid is returned via the conduit 10 to the liquid reservoir which is situated upstream of the conduit 1. The bone tissues are discharged by the conduit 11 after opening the valve 12.

It is of course easy to automate the introduction of the ground skeletons into the separating vessel, the discharge of the cartilages and of the bone tissues by any known means.

Trial 1

For this trial and for the next trial, the experimental system for separating and extracting cartilages, corresponding to FIG. 1, comprises a translucent Plexiglass separating vessel with a capacity of 15 liters.

The pump has a variable output which can be adjusted from 0 to 3 500 liters per hour.

For the purposes of the experiment, the bone tissues are discharged at the end of each experiment by aspirating them with a flexible pipe connected to a suction pump.

In this first trial, turkey skeletons, which are by-products from a slaughterhouse which undertakes the "cutting" of these fowl, are collected.

They are then ground in a mincer commonly used in the industry for prepared meat products, also called a "cutter", until particles of less than one centimeter are obtained.

The separating liquid is brine containing 30% of cooking salt.

The pump is adjusted such that the flow rate of the brine in the separating vessel is 1 500 liters per hour.

After introducing into the separating system a total weight of one kilogram of ground skeletons, 32 grams of cartilages were recovered at the end of the experiment.

Trial 2

10 kilograms of chicken skeletons which had been coarsely ground in a poultry breeding center are collected.

They are again ground in a mincer so as to reduce the size of the particles to less than one centimeter.

For this experiment, tap water is used as separating liquid.

The capacity of the pump is adjusted such that water goes through the separating vessel at the rate of 3 000 liters per hour.

After the experiment, which was performed on the 10 kilograms of ground chicken skeletons, it was possible to separate and extract 550 grams of cartilages.

Trial 3

Starting with cartilages obtained in trial 2, the active ingredients which can be used in human and animal dietetic nutrition, in human and veterinary pharmacy or in cosmetology, were evaluated.

The collagens were assayed according to the method used by the Laréal laboratory, 56250 Saint Nolff, France, and accredited by the French Accreditation Committee, better known by the name COFRAC (reference COFRAC: CC 70; laboratory reference: AN 85; accreditation number: 1–285).

The hexosamines were assayed according to the method described in "Techniques d'analyse et de contrôle dans les industries agro-alimentaires", 1981, Volume 4, pages 95–97, published by Technique et Documentation, Lavoisier, APRIA.

The glycosaminoglycans, which are expressed in the form of chondroitin sulfate, were extracted according to the method of L. Roden et al (In "Methods in Enzymology. Vol. XXVIII, Complex Carbohydrates, Part B" Edited by V. Ginsburg, Academic Press, 1972, pages 73–140), and assayed according to the method described in Pharmeuropa, 1997, Vol. 9, No., 12, pages 193–196.

The results obtained were the following, expressed as a percentage by weight of wet cartilages:

collagens: 8.80%, hexosamines: 0.99%, glycosaminoglycans: 2.32%.

What is claimed is:

1. A method for separating and extracting cartilages of avian origin, comprising the steps of:
    a) grinding avian skeletons until a mean particle size of about 1 centimeter or less is obtained; and
    b) separating and extracting said cartilages from said ground avian skeletons by a flow of edible liquid circulating in a separating vessel.

2. The method according to claim 1, characterized in that the flow of edible liquid circulating in a separating vessel has an ascending vertical component.

3. The method according to claim 1, characterized in that the separating liquid is water or an edible brine.

4. The method according to claim 1, wherein the avian skeletons are poultry skeletons.

5. The method according to claim 4, wherein the poultry skeletons are chicken skeletons.

* * * * *